(12) United States Patent
Bommarito et al.

(10) Patent No.: US 10,161,895 B2
(45) Date of Patent: Dec. 25, 2018

(54) ELECTRONIC MOISTURE SENSOR

(71) Applicant: 3M INNOVATIVE PROPERTIES COMPANY, St. Paul, MN (US)

(72) Inventors: G. Marco Bommarito, Stillwater, MN (US); Justin M. Johnson, Hudson, WI (US); Kevin D. Landgrebe, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 150 days.

(21) Appl. No.: 14/976,506

(22) Filed: Dec. 21, 2015

(65) Prior Publication Data

US 2016/0178553 A1 Jun. 23, 2016

Related U.S. Application Data

(60) Provisional application No. 62/095,818, filed on Dec. 23, 2014.

(51) Int. Cl.
*G01N 27/22* (2006.01)

(52) U.S. Cl.
CPC .......... *G01N 27/225* (2013.01); *G01N 27/223* (2013.01)

(58) Field of Classification Search
CPC ............................ G01N 27/225; G01N 27/223
See application file for complete search history.

(56) References Cited

U.S. PATENT DOCUMENTS

| | | |
|---|---|---|
| 4,049,121 A | 9/1977 | White |
| 4,406,827 A | 9/1983 | Carim |
| 4,554,924 A | 11/1985 | Engel |
| 4,848,353 A | 7/1989 | Engel |
| 5,489,624 A | 2/1996 | Kantner et al. |
| 5,745,039 A | 4/1998 | Hof et al. |
| 6,038,464 A | 3/2000 | Axelgaard et al. |
| 6,075,178 A | 6/2000 | La Wilhelm et al. |
| 6,709,716 B2 | 3/2004 | Uy et al. |
| 6,774,800 B2 | 8/2004 | Friedman et al. |
| 6,905,763 B2 | 6/2005 | Crandall et al. |
| 7,030,631 B1 | 4/2006 | Jennings |

(Continued)

FOREIGN PATENT DOCUMENTS

| | | |
|---|---|---|
| EP | 2 009 432 | 12/2008 |
| EP | 2 437 795 | 4/2012 |

(Continued)

OTHER PUBLICATIONS

Gao et al., Development of a novel moisture sensor based on superabsorbent poly(acrylamide)-montmorillonite composite hydrogels, 2001, Journal of Materials Science 36, pp. 4567-4571.*

*Primary Examiner* — Hezron E Williams
*Assistant Examiner* — David Z Huang

(57) ABSTRACT

Moisture sensors that include a resonant circuit having a capacitive element and an inductive element, wherein the inductive element acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer.

20 Claims, 2 Drawing Sheets

(56) References Cited

U.S. PATENT DOCUMENTS

| | | |
|---|---|---|
| 7,456,744 B2 | 11/2008 | Kuhns et al. |
| 7,948,380 B2 | 5/2011 | Kuhns et al. |
| 7,999,023 B2 | 8/2011 | Menon et al. |
| 2004/0043369 A1 | 3/2004 | Pawar et al. |
| 2004/0070510 A1 | 4/2004 | Zhang et al. |
| 2006/0174693 A1 | 8/2006 | Chen et al. |
| 2008/0061802 A1* | 3/2008 | Alimi ............ G01N 27/225 324/689 |
| 2009/0124990 A1 | 5/2009 | Feldkamp et al. |
| 2010/0100026 A1 | 4/2010 | Morris |
| 2010/0139880 A1 | 6/2010 | Vuolanto |
| 2011/0217573 A1* | 9/2011 | Kritzer ............ G01F 23/263 429/61 |
| 2012/0000284 A1 | 1/2012 | Yokoyama et al. |
| 2013/0036802 A1 | 2/2013 | Johnson et al. |
| 2013/0041334 A1 | 2/2013 | Prioleau et al. |
| 2016/0178538 A1 | 6/2016 | Bommarito et al. |

FOREIGN PATENT DOCUMENTS

| | | |
|---|---|---|
| GB | 2 178 539 | 2/1987 |
| JP | 7-174726 | 7/1995 |
| WO | WO 1997/29789 | 8/1997 |
| WO | WO 1998/23920 | 6/1998 |
| WO | WO 2004/004615 | 1/2004 |
| WO | WO 2008/089189 | 7/2008 |
| WO | WO 2010/14119 | 12/2010 |

\* cited by examiner

ELECTRONIC MOISTURE SENSOR

CROSS REFERENCE TO RELATED APPLICATIONS

This application claims priority to U.S. Provisional Patent Application No. 62/095,818, filed Dec. 23, 2014, the disclosure of which is incorporated by reference in its entirety herein.

BACKGROUND

Moisture sensors are used, for example to determine the presence or absence of certain amounts of moisture in the vicinity of the sensor. Moisture sensors are needed in various applications, for example to determine whether an item has been exposed to moisture, whether there is too much or too little moisture in an environment, etc. Various moisture sensors have been created, including chemical moisture sensors, however, chemical sensors can cause environmental concern, and often require close inspection to determine the output of the sensor. Electronic moisture sensors allowing for remote sensing of moisture conditions have been developed using technologies such as radio frequency identification (RFID) circuitry and electronic article surveillance (EAS) tags, but remain imperfect. Many RFID and EAS sensor technologies require complex interactions of different variables or are costly to manufacture. Some can only provide indication of the presence of liquid water (and not merely a moist atmosphere), while others rely on resonant frequency shifts, which can be adversely affected by temperature conditions and require circuit tuning. There remains a need for a simple, reliable, cost-effective moisture sensor that can provide remote indication of moisture conditions.

SUMMARY

The present disclosure is directed to devices, methods, and systems involving remote sensing of moisture conditions based on resonant circuit technology. The disclosed devices, methods, and systems advantageously allow remote sensing of moisture, both in a liquid and a vapor state, without complex circuit tuning or complex circuit construction.

Disclosed herein are moisture sensors that include a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer.

Also disclosed is a system that includes a moisture sensor including a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer; and a reader configured to transmit a reader radio frequency signal to the resonant circuit of the moisture sensor at or near the resonant frequency of the resonant circuit, and wherein the reader is further configured to receive a moisture sensor signal transmitted by the resonant circuit.

Also disclosed is a method that includes sequential steps: (a) exposing a moisture sensor to a moist atmosphere, wherein the moisture sensor includes a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer; (b) transmitting a reader radio frequency signal from a reader to the resonant circuit of the moisture sensor at the resonant frequency of the resonant circuit to produce a moisture sensor signal, wherein the reader is configured to transmit a reader radio frequency signal to the resonant circuit of the moisture sensor at or near the resonant frequency of the resonant circuit; (c) receiving, with the reader, a moisture sensor signal from the moisture sensor and generating, with the reader, an indication signal based on the moisture sensing signal received from the resonant circuit, wherein the reader is further configured to receive a moisture sensor signal transmitted by the resonant circuit and generate an indication signal based on the moisture sensor signal received; and (d) determining a level of moisture within the moist atmosphere based on the signal generated by the reader.

Also disclosed is a method that includes receiving, by a receiving device, a moisture sensor signal produced by a moisture sensor, the moisture sensor including a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer; and determining the moisture conditions to which the polymeric layer is exposed based on the moisture sensor signal received by the receiving device.

The above summary is not intended to describe each disclosed embodiment of every implementation of the present invention. The details of one or more embodiments of the invention are also set forth in the description below. Other features, objects, and advantages of the invention will be apparent from the description and from the claims.

DETAILED DESCRIPTION

Figure 1:
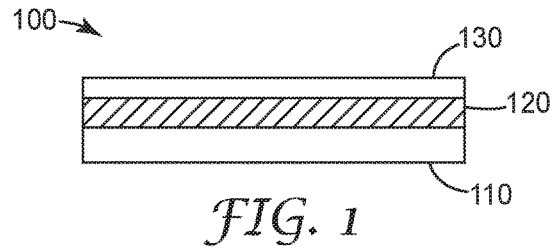
FIG. 1 is a cross-sectional view of one embodiment of a disclosed moisture sensor.

In the following description of illustrative embodiments, reference is made to the accompanying figures which form a part hereof, and in which are shown, by way of illustration, specific embodiments. It is to be understood that other embodiments may be utilized and structural changes may be made without departing from the scope of the present disclosure.

As used herein and in the appended claims, the singular forms "a," "and," and "the" include plural referents unless the context clearly dictates otherwise. Thus, for example, reference to "a spacer" includes a plurality of spacers (unless otherwise expressly indicated) and equivalents thereof known to those skilled in the art.

As used herein, "humidity," "wetness," and "moisture" are used interchangeably.

Unless otherwise specified, as used herein, all relative humidity values refer to relative humidity, as measured at room temperature (between 22° C. and 28° C.).

Unless otherwise indicated, all numbers expressing quantities of ingredients, viscosities, humidity values, etc., in the specification and claims are to be understood as being modified by the term "about" in all instances. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters set forth herein are approximations, the numerical values set forth in the specific examples are reported as precisely as possible. Any numerical values, however, inherently contain certain errors necessarily resulting from the standard deviation found in their respective testing measurements.

The present disclosure generally relates to the field of electronic moisture sensors, and more specifically to moisture sensors comprising a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer.

While electronic sensors for detecting moisture exist, many rely on the presence of liquid water in order to trigger detection of the presence of moisture. For instance, a drop of water, visible to the human eye, must often be on currently available sensors in order for them to signal that moisture is present. Applicants have surprisingly found that the electronic moisture sensors described herein are capable of detecting not just liquid water, but also relative humidity in an environment. Thus, the electronic moisture sensors described herein are more sensitive than the electronic moisture sensors previously available. In addition, the sensors described herein can be adjusted to detect specific levels of moisture as necessary for the intended application, making them useful across many technologies and fields. Additionally, the sensors can also be adjusted to require the presence of liquid water for detection. In these embodiments, the sensors are superior to currently available sensors because they do not require circuit tuning and/or additional circuitry such as reference circuits.

FIG. 1 is a cross-sectional view of one embodiment of a disclosed moisture sensor 100. Moisture sensor 100 can include a resonant circuit 110, a conditionally conductive layer 130, and an optional insulative layer 120 disposed between the resonant circuit and the conditionally conductive layer.

Conditionally conductive, when used herein refers to conditionally electrically conductive. It should also be noted that the conditionally conductive layer can be referred to as conditionally electrically resistive. Conditionally conductive layers may have a first level of conductivity when exposed to a first condition or set of conditions (e.g., moisture conditions) and a second level of conductivity when exposed to a second condition or set of conditions (e.g., moisture conditions). A condition, set of conditions, or more specifically moisture conditions can refer to relative humidity, the presence of water as a liquid, or some combination thereof. For example, in some embodiments, a conditionally conductive layer may have a lower level of conductivity when exposed to lower levels of relative humidity, and a higher level of conductivity when exposed to higher levels of relative humidity. For example, in some embodiments, a conditionally conductive layer may have a lower level of conductivity when exposed to lower levels of relative humidity, no liquid water present on the conditionally conductive layer, or a combination thereof, and a higher level of conductivity when exposed to higher levels of relative humidity, when there is liquid water present on the conditionally conductive layer, or some combination thereof.

In some embodiments, a conditionally conductive layer can respond to a change in moisture conditions. For example, a conditionally conductive layer can change from less conductive (for example, non-conductive) to more conductive (for example, conductive) when the relative humidity of the surroundings change. For example, a conditionally conductive layer can change from less conductive to more conductive (or vice versa) when the relative humidity ("RH") changes some amount or reaches a threshold level of moisture. The change in the relative humidity that alters the conditionally conductive layer from less conductive to more conductive may translate into a change in relative humidity that a moisture sensor containing the conditionally conductive layer can detect.

In some embodiments, the conditionally conductive layer can include one or more polymeric materials, in such embodiments it can be referred to as a conditionally conductive polymeric layer. In some embodiments, a conditionally conductive layer can include more than one layer, e.g., a conditionally conductive layer can be made up of more than two layers of materials (one or more different materials) that together have the properties of a conditionally conductive layer. Illustrative materials that can be used to construct conditionally conductive polymeric layers can include for example, hydrogels, and polyelectrolytes. In some embodiments, a material (e.g., a polymer) that is electrically conditionally conductive can be utilized for the conditionally conductive layer. In some embodiments, a material that can be made to be electrically conditionally conductive can be utilized. A material, such as a polymer can be made to be conditionally conductive, for example, by the inclusion of a salt. For example, a salt such as sodium chloride (NaCl), potassium chloride (KCl), lithium chloride (LiCl), or any combination thereof can be added to a polymer (or a different material) to render the material conditionally conductive or to enhance the conductivity. In some embodiments, an amount of a salt not greater than 5 wt %, in some embodiments an amount of salt not greater than 3 wt %, and in some embodiments not greater than 2 wt % can be utilized.

An illustrative class of conditionally conductive materials includes hydrogels. As used herein, hydrogels can include hydrophilic polymeric network materials that can absorb large volumes of water without dissolving. It is possible to create hydrogels with varying amounts of water from just a few percent to over 90 percent. The total absorbency and swelling capacity are controlled by the type and degree of cross-linkers used to make the gel. Low-density cross-linked gels generally have a higher absorbent capacity and swell to a larger degree, resulting in soft and sticky materials. High cross-link density polymers exhibit lower absorbent capacity and swell, resulting in firmer materials capable of holding their shape under a mechanical stress. Hydrogels can be formed from natural or synthetic polymers. Compositions of synthetic hydrogels commonly include: polyethylene oxide, polyAMPS, polyvinylpyrrolidone, polyvinyl alcohol, polyacrylamide, polyacrylonitrile, sodium polyacrylate, and other acrylate polymers and copolymers with a significant amount of hydrophilic groups. Compositions of natural hydrogels commonly include: agarose, methylcellulose, hyaluronan, and other naturally derived polymers. Hydrogels can be cross-linked by several methods (for example by exposure to heat, light or another source of actinic radiation) to varying degrees in order to increase their mechanical robustness.

As used herein, a hydrogel can also include colloidal gels with water as the primary dispersion medium that can be considered hydrogels. For example, hydrocolloids can be considered to be a hydrogel. A hydrocolloid is a colloidal system where the colloid particles are hydrophilic polymers uniformly dispersed in water. Depending on the quantity of water, the hydrocolloid can either be a gel or a liquid (sol) and can be either irreversible (single-state) or reversible. For example, agar can exist in a gel and solid state, and alternate between states with heat. Many hydrocolloids are derived from natural sources, for example: agar, gelatin and pectin. Other main hydrocolloids are xanthan gum, gum arabic, guar gum, locust bean gum, cellulose derivatives as carboxymethyl cellulose, alginate and starch. Hydrocolloids are used primarily as a viscosity modifier.

In some embodiments, relevant hydrogels may include those where the water is absorbed and desorbed reversibly. Such hydrogels can be useful in applications which generally include a stage of wetness where moisture or liquid water is present, and a drying step. Thus, it is important for an electronic moisture sensor designed for such an application to include a moisture sensing element that can reversibly detect the presence of water.

An illustrative class of conditionally conductive materials includes polyelectrolytes or polysalts. As used herein, polyelectrolytes are polymers whose repeating units include an electrolytic moiety. Polyelectrolytes are composed of polycations or polyanions or a combination of both. In the presence of water polycation and/or polyanion groups disassociate making the polymer charged. Polyelectrolytes embody the charge properties of typical electrolytes and the rheological properties of typical polymers. The physical properties of polyelectrolyte solutions with water are strongly affected by the degree of charging and the conformation of the polymer. The extent of charging upon dissociation alters the electrical conductivity of the polyelectrolyte. Furthermore, the chain or structural conformation attained by the polyelectrolyte as a result of dissociation and a given degree of charging, will affect many bulk properties (viscosity, turbidity, etc.). Both natural and synthetic polyelectrolytes can be used. Some of the hydrocollloids mentioned above can be considered polyelectrolytes (e.g., pectin, carrageenan, alginates, and carboxymethyl cellulose). Naturally occurring biological polyelectrolytes can include, for example, polypeptides, glycosaminoglycans, and DNA. Examples of synthetic polyelectrolytes include polysodium styrene sulfonate and polyacrylic acid.

Polyelectrolytes may also be used to create more complicated materials known as polyelectrolyte multilayers (PEMs) that can be used as the conditionally conductive layer for some embodiments herein. These thin films are constructed using a layer-by-layer deposition technique in which a given substrate is dipped back and forth between dilute baths of positively and negatively charged polyelectrolyte solutions. During each dip a small amount of polyelectrolyte is adsorbed and the surface charge is reversed, allowing the gradual and controlled build-up of electrostatically cross-linked films of polycation-polyanion layers. These films can also be constructed by substituting charged materials (for example, charged nanoparticles or clay platelets) instead of or in addition to one of the polyelectrolytes. The films can also be created by exploiting hydrogen bonding between polyelectrolytes rather than electrostatic interactions. A useful uniqueness of polyelectrolyte multilayers is that they can be potentially created as a coating directly on an article of interest.

The dielectric properties of conditionally conductive materials, such as hydrogels can vary depending on the amount of water that is absorbed thereby. Such changes in dielectric properties can lead to referring to them as conditionally conductive materials. Changes in these dielectric properties (e.g., electrical conductance) can be measured using several methods. For example, the permittivity (dielectric constant and dielectric loss) of a medium can be measured using ASTM D150 over a given range of frequency, e.g., a range of frequency that is relevant. More specifically, using the ASTM D150 method one can measure the complex permittivity of a conditionally conductive layer material (e.g., a hydrogel) as a function of frequency and water content of the material. The complex permittivity describes how much electric flux is generated per unit charge in the material: the higher the permittivity the higher the electric flux per unit charge. A conditionally conductive layer having a given composition at a given measurement frequency, will have an increasing permittivity with increasing amounts of absorbed water. At some point the absorbed water in the material will be high enough to create a complex permittivity corresponding to an electric flux generated in the material large enough to shield the resonant frequency of a resonant circuit associated with that conditionally conductive layer. At that point the resonant circuit will likely no longer be detectable by a reader or the resonant circuit will no longer be able to receive a radio frequency signal transmitted from a source (e.g., reader) external to the moisture sensor at the resonant frequency of the moisture sensor's resonant circuit.

In some embodiments, a relevant operational frequency, e.g., the frequency at which the resonant circuit resonates, can range from 100 kHz to 20 MHz. This is the range of frequencies that would be used to interrogate the resonant circuit using conventional reader instrumentation. As used herein, to interrogate includes transmitting a RF signal at or near the resonant frequency of the resonant circuit to produce a moisture sensor signal, and receiving the moisture sensor signal transmitted by the resonant circuit, which can include, in some embodiments, a non-signal or a RF signal. Over such an operational frequency range, and with increasing amounts of absorbed water, the complex permittivity of useful conditionally conductive materials varies predominantly in the imaginary component of the permittivity or equivalently varies predominantly in conductivity. Conductivity is related to the imaginary component of permittivity according to the following equation:

$$\sigma = 2\pi f \varepsilon_0 \varepsilon''$$

where $\sigma$ is the conductivity, f is the operational frequency $\varepsilon_0$ is the permittivity of vacuum ($8.85 \times 10^{-12}$ F/m) and $\varepsilon''$ is the imaginary permittivity of the material for a given composition and amount of adsorbed water.

Conductivities of materials that may be useful can be characterized using a test method, for example ASTM D150 at a relevant frequency and at relevant relative humidities. In theory, there need not be an upper limit on the conductivity of a useful material at a relative humidity where it is desired that the conditionally conductive layer shield the resonant circuit. The limit of the conductivity of a useful material at a relative humidity where it is desired that the conditionally conductive layer shield the resonant circuit is a level of conductivity high enough to cause the shielding. In theory, there need not be a lower limit on the conductivity of a useful material at a relative humidity where it is desired that the conditionally conductive layer not shield the resonant circuit. The limit of the conductivity of a useful material at a relative humidity where it is desired that the conditionally conductive layer not shield the resonant circuit is a level of conductivity low enough to not cause the shielding.

In some embodiments, useful conditionally conductive materials may include materials (e.g., hydrogels) with conductivities as low as 0.0001 S/m, in some embodiments as low as 0.001 S/m, or in some embodiments as low as 0.1 S/m as measured using a test method such as ASTM D150 over a frequency range of 100 kHz to 20 MHz, in environments. In some embodiments, useful conditionally conductive materials may include materials (e.g., hydrogels) with conductivities that are infinitely high, in some embodiments as high as 50 S/m, in some embodiments as high as 5 S/m, in some embodiments as high as 0.8 S/m, or in some embodiments as high as 0.5 S/m as measured using a test method such as ASTM D150 over a frequency range of 100 kHz to 20 MHz, in environments. In some embodiments, useful conditionally conductive materials may include materials (e.g., hydrogels) with conductivities ranging from 0.0001 S/m to 50 S/m as measured using a test method such as ASTM D150 over a frequency range of 100 kHz to 20 MHz, in environments varying from 15% to 85% relative humidity.

Illustrative types of materials that can be utilized for the conditionally conductive layer includes hydrogels. Both synthetic and natural hydrogels can be utilized herein. Illustrative specific types can include those found in U.S. Pat. Nos. 4,406,827; 6,038,464; 4,554,924; 5,489,624; 6,709,716; and 7,999,023 for example, the disclosures of which are incorporated herein by reference thereto.

Illustrative specific types of conditionally conductive polymers can include copolymers of hydrogen bond donating monomers and hydrogen bond accepting monomers. For example, specific types of conditionally conductive polymers can include a polymer that includes copolymers of acrylic acid and N-vinylpyrrolidone. Exemplary specific conditionally conductive hydrogels can include, for example the hydrogel adhesive of AG603-6 sensing gel (available from AmGel Technologies a division of Axelgaard Manufacturing Company Ltd. Of Fallbrook, Calif.), the hydrogel adhesive of 3M™ RED DOT™ Resting EKG Electrode 2330 (3M Company, St. Paul, Minn.).

Conditionally conductive layers may also have optional other properties. For example, conditionally conductive polymeric layers may have properties that allow them to function as an adhesive, for example a pressure sensitive adhesive. Conditionally conductive polymers that also have adhesive properties may be beneficial in that they can aid in forming the moisture sensor by maintaining the conditionally conductive layer in contact with adjacent portions of the moistures sensor, with adjacent structures, or both. Conditionally conductive polymeric layers may be modified before use, before being formed into moisture sensors, or after being formed into moisture sensors.

Disclosed moisture sensors (such as that illustrated in FIG. 1) can also include an insulative layer 120. As seen in FIG. 1, the optional insulative layer 120, if present is located between the conditionally conductive layer 130 and the resonant circuit 110. The insulative layer can function to electrically insulate the resonant circuit from the conditionally conductive layer, from water that may be present in the conditionally conductive layer, or both. In some embodiments, the insulative layer may also have adhesive properties. Insulative layers that also have adhesive properties may be beneficial in that they can aid in forming the moisture sensor by maintaining the insulative layer in contact with adjacent portions of the moistures sensor.

In some embodiments, the insulative layer 120 can include any electrically insulative material. In some embodiments, the insulative layer 120 can function to prevent electrical shorting of the resonant circuit itself (once exposed to moisture) or shorting between the resonant circuit and the conditionally conductive layer. In some embodiments, the insulative layer can be a material that has is sufficiently electrically insulative to have a resistance such that the resistance is greater than the volume resistivity of the conditionally conductive layer. In some embodiments, the insulative layer can have an electrical conductivity of less than $1 \times 10^{-8}$ S/m, in some embodiments less than 0.0001 S/m, or in some embodiments less than 0.001 S/m. In some embodiments, the insulative layer can include a material that has adhesive properties and an electrical conductivity of not less than 0.001 S/m. In some embodiments, the insulative layer 120 can comprise air, paper, Teflon, glass, polyethylene (PET), a non-conductive adhesive, or combinations thereof, for example.

Figure 2:
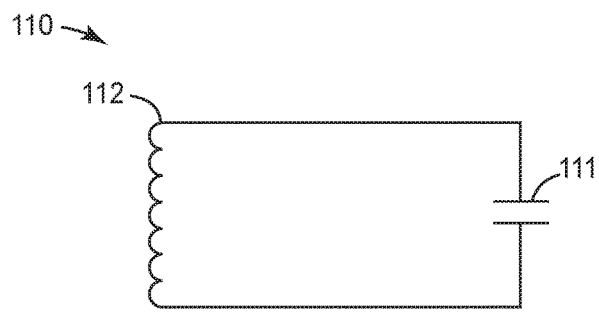
FIG. 2 is a schematic diagram illustrating one embodiment of a disclosed resonant circuit useful in disclosed moisture sensors.

Disclosed moisture sensors, such as that depicted in FIG. 1 as 100 also include a resonant circuit 110. FIG. 2 is a schematic diagram more specifically illustrating an embodiment of a resonant circuit 110 that can be used in disclosed moisture sensors. Resonant circuit 110 includes a capacitive element 111 and an inductive element 112. In some embodiments, a resistive element may also be included in the resonant circuit 110. It is to be understood that, while not shown, the resonant circuit will have some amount of parasitic resistance naturally present in the resonant circuit 110. Circuit 110 is designed to resonate at a specific frequency based on the identities and characteristics of the circuit components 111 and 112. The inductive element 112 acts as an antenna used to receive, reflect, or transmit electromagnetic energy, such as radio frequency (RF)

energy. In some applications, additional circuitry (not shown) can be coupled to the resonant circuit 110, such as, e.g., circuitry for outputting an identification code via the antenna. Devices that are capable of transmitting a code are typically referred to as RFID devices. Devices without the additional circuitry for outputting the ID code are often referred to as EAS device.

Illustrative commercially available products that can be utilized as resonant circuits in disclosed devices can include, for example those available from ALL-TAG Corporation (Boca Raton, Fla.), Avery Dennison Corporation (Glendale, Calif.), Best Security Industries (Delray Beach, Fla.), Nedap N.V. (Netherlands), TAGIT EAS (Canada), SL595P sensor labels commercially available from SenTech EAS Corporation (Pompano Beach, Fla.), and 3M™ ISO RFID tags available from 3M (St. Paul, Minn.). Readers for use with such illustrative tags are known to those of skill in the art and are commercially available. An illustrative commercially available reader is a SenTech 9.5 MHz Portable Hand Verifier, model STC311 from SenTech EAS Corporation (Pompano Beach, Fla.).

Figure 3:
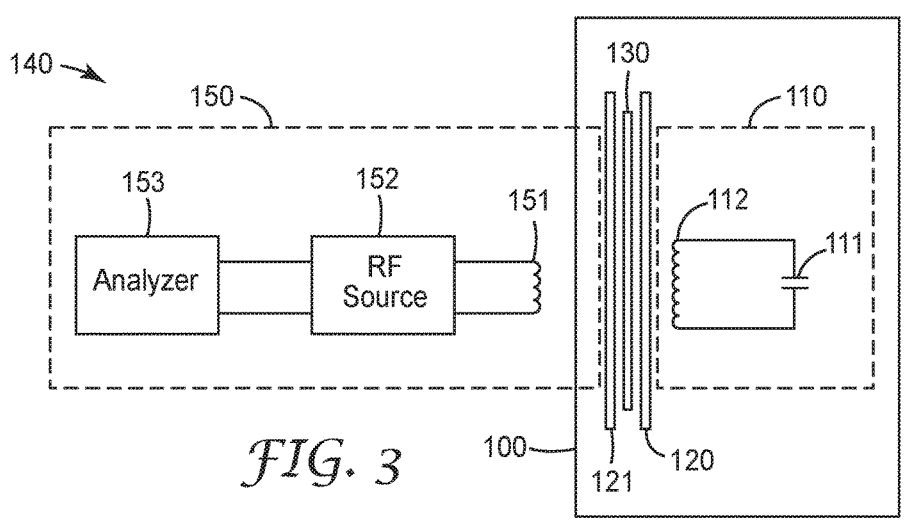
FIG. 3 is a schematic diagram of one embodiment of a disclosed remote sensing system.

FIG. 3 is a schematic diagram of one embodiment of a disclosed remote sensing system 140. The remote sensing system 140 includes a reader 150 and a moisture sensor 110 as described above. The reader can include a radio frequency (RF) source 152 and an analyzer 153. The reader 150 can also include a reader inductive element 151 that serves as an antenna to transmit an RF signal to the resonant circuit 110. The moisture sensor, as discussed above includes a resonant circuit 110, which includes at least a capacitive element 111 and an inductive element 112, which absorbs and reflects RF energy near the resonant frequency of the resonant circuit. In some embodiments, the reader can be configured to detect a signal at the frequency at which the resonant circuit 110 transmits. An insulative layer 120 can be disposed between the resonant circuit 110 and the conditionally conductive layer 130, while an optional secondary insulative layer 121 can be disposed between the reader 150 and the conditionally conducive layer 130. In some embodiments, the optional secondary insulative layer can have properties similar to the insulative layer 120, and can include, for example air, paper, Teflon, glass, polyethylene (PET), a non-conductive adhesive, or combinations thereof. In some embodiments, the optional secondary insulative layer can comprise air.

Figure 4:
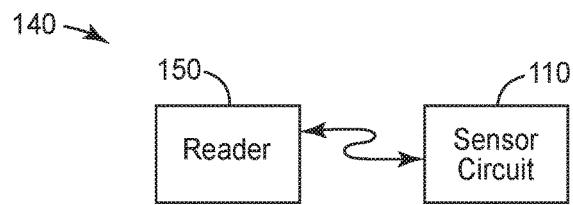
FIG. 4 is a block diagram illustrating one embodiment of a disclosed remote sensing system.

A remote sensing system 140 including resonant circuit 110 and reader 150 is depicted in the block diagram of FIG. 4. In some embodiments, the reader 150 receives a signal produced by the resonant circuit 110. This occurs if, once the reader sends a signal to the resonant circuit, the resonant circuit receives that signal and responds, by resonating, and that resonance is then detected by the reader. This condition can be referred to as a signal or detectable. The reader does not receive a signal produced by the resonant circuit 110 if, once the reader sends a signal to the resonant circuit, the resonant circuit does not receive that signal because it is shielded from the signal by the conditionally conductive layer, and therefore does not resonate and thus does not produce a signal to be received by the reader. This condition can be referred to as a non-signal, silence, or undetectable. In some embodiments, the reader does not receive a signal produced by the resonant circuit 110 if, once the reader sends a signal to the resonant circuit, the resonant circuit resonates but the moisture sensor signal produced by the resonating circuit is shielded then by the conditionally conductive layer and thus the reader does not receive the moisture sensor signal. This condition can also be referred to as a non-signal, silence, or undetectable. In some embodiments, disclosed devices, systems and methods do not rely upon detecting a shift in the resonant frequency of the resonant circuit response. In some embodiments, disclosed devices, systems and methods rely on detecting whether the resonant circuit is shielded or not.

Disclosed moisture sensors and remote sensing systems may be utilized to detect moisture conditions or changes in moisture conditions. When a disclosed moisture sensor is located in surroundings subjected to changes in moisture conditions or humidity conditions, the conditionally conductive layer of the moisture sensor will absorb moisture or water from the surroundings (or desorb to the surroundings in the case of detecting a decrease in relative humidity), causing a change in the conductivity of the conditionally conductive layer. In some embodiments, the change in the conductivity of the conditionally conductive layer shields the resonant circuit from receiving signals that might result in resonating or the resonant circuit (e.g. radio frequency signal from the reader) and thus results in no signal being sent back to the reader (e.g. a non-signal). In some embodiments, the change in the conductivity of the conditionally conductive layer prevents or diminishes a signal being sent back to the reader from the resonant circuit. The sensitivity of disclosed remote sensing systems are therefore dependent on the amount of water that needs to be absorbed by the conditionally conductive layer to change it from less conductive to more conductive (or vice versa) or more specifically to make the resonant circuit go from "visible" (or not shielded) to "not visible" (or shielded) to the reader. As such, moisture sensors to detect different amounts of relative humidity change, or changes in relative humidity at different levels of relative humidity could be fabricated by choosing materials or different types of materials for the conditionally conductive layer.

In some embodiments, disclosed moisture sensors, remote sensing systems, or both can detect a moisture condition change, measured by percent relative humidity (% RH) that is less than 10% RH. In some embodiments, disclosed moisture sensors, remote sensing systems, or both can detect a moisture condition change of 5% RH. The percent change in the relative humidity that can be detected may change as the absolute relative humidity of the surrounding conditions change. For example, in some embodiments, a moisture condition change that is less than 10% RH can be detected when the surrounding conditions are at least 50% RH. For example, in some embodiments, a moisture condition change that is 5% RH can be detected when the surrounding conditions are at least 50% RH.

In some embodiments, disclosed moisture sensors, remote sensing systems, or both can detect a threshold level of moisture. Threshold levels can be considered maximum moisture levels or minimum moisture levels, depending on whether a moisture sensor is to be used as determining if something is "wet" or "dry". In some embodiments, a moisture sensor, remote sensing system, or both can detect a level of relative humidity that is above a certain level, e.g., a conditionally conductive layer can have its conductivity changed. For example, a moisture sensor, remote sensing systems, or both can detect a relative humidity that is at least 55% relative humidity, at least 58% relative humidity, or at least 60% relative humidity. In some embodiments, a moisture sensor, remote sensing system, or both can detect a level of relative humidity that is below a certain level, e.g., a conditionally conductive layer can have its conductivity changed. For example, a moisture sensor, remote sensing systems, or both can detect a relative humidity that is not greater than 60% relative humidity, not greater than 58% relative humidity, or not greater than 55% relative humidity. It should also be noted that disclosed moisture sensors, remote sensing systems, or both can be utilized as reversible or non-reversible moisture sensors or systems.

In some embodiments, moisture sensors can include conditionally conductive layers that can change from a first level of conductivity to a second level of conductivity when exposed to a relative humidity ranging from 55% to 95% at room temperature. In some embodiments, moisture sensors can include conditionally conductive layers that can change from a first level of conductivity to a second level of conductivity when exposed to a relative humidity that is at least 55%. In some embodiments, moisture sensors can include conditionally conductive layers that can change from a first level of conductivity to a second level of conductivity when exposed to a relative humidity that is at least 58%.

Figure 5:
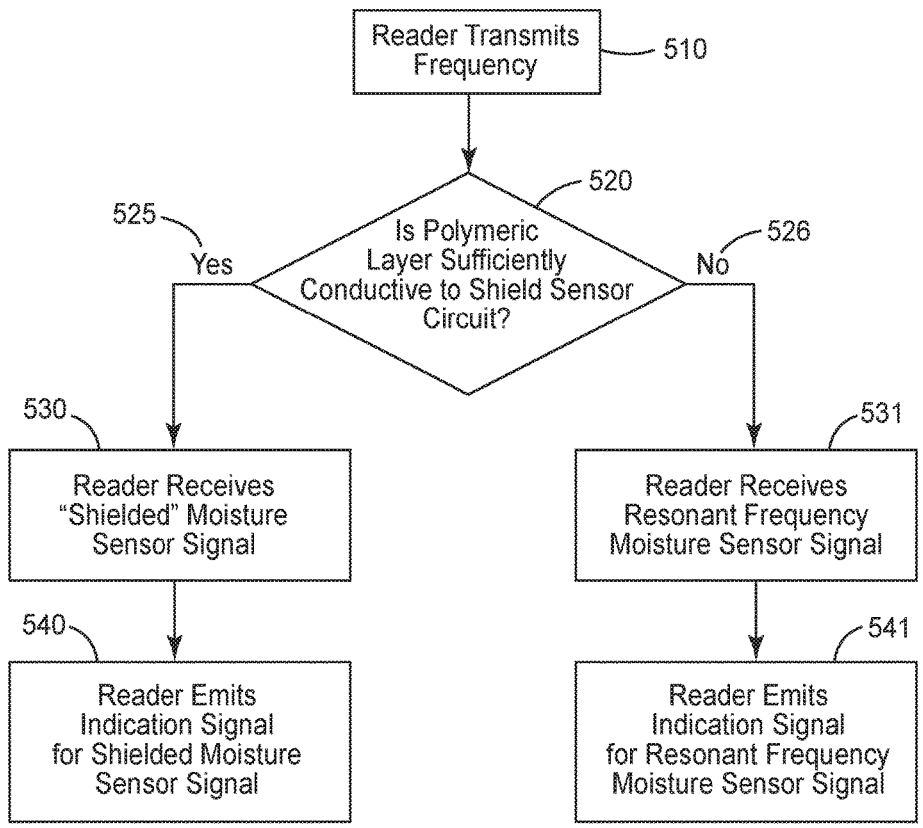
FIG. 5 is a flowchart illustrating one embodiment of a disclosed method.

The flowchart of FIG. 5 further illustrates exemplary moisture detection methods that can be implemented utilizing disclosed readers, disclosed moisture sensors, or both. In some embodiments, once a moisture sensor has been exposed to a moist atmosphere, the reader may be used in conjunction with the moisture sensor to determine the level of moisture within the moist atmosphere. In the first step following exposure of the moisture sensor to a moist environment, 510, the reader transmits a radio frequency (RF) signal at or near the resonant frequency of the resonant circuit to excite a resonant circuit within a moisture sensor, i.e. cause the resonant circuit to resonate at or near its resonant frequency. The excitation, or resonating, of the resonant circuit leads to the production of a moisture sensor signal, based on whether or not the conditionally conductive layer is sufficiently conductive to shield the resonant circuit, 520, in response to a signal from the reader. For example, if the conditionally conductive layer is sufficiently conductive to prevent or diminish the resonant circuit's resonance, 525, either by shielding the RF signal transmitted by the reader such that the resonant circuit does not receive the reader's RF signal or receives too diminished of a signal to result in resonating of the resonant circuit, or by shielding any resultant resonation of the resonant circuit (and resultant signal) from reaching the reader, the reader receives a "shielded" moisture sensor signal from the moisture sensor, 530, indicating that the conditionally conductive layer is shielding the resonant circuit. This "shielded moisture sensor signal can, in some embodiments, include a non-signal, or null. The reader can then emit an indication signal for "shielded" moisture sensor signal 540. If the conditionally conductive layer is not sufficiently conductive to shield the resonant circuit 526, the resonant circuit will resonate in response to the signal received from the reader and transmit a signal at or near the resonant frequency of the resonant circuit back to the reader such that the reader receives a resonant frequency from the moisture sensor 531, indicating that the conditionally conductive layer is not shielding the resonant circuit. The reader then generates an indication signal for the moisture sensor signal 541, e.g., a "non-shielded" moisture sensor signal. An emitted signal from the reader may be one that is audible or visible to a user, or in some cases, lack of an audible or visible signal may also signal a condition to a user.

In some embodiments, a "shielded" moisture sensor signal may comprise a non-signal, or null. In some embodiments, a reader may generate an indication signal which is a non-signal or silence in response to a "shielded" moisture sensor signal. In some embodiments, a "shielded" moisture sensor signal may comprise a radio frequency signal that is diminished from the resonant frequency of the moisture sensor's resonant circuit. In some embodiments, a reader may generate an audible or visible indication signal in response to a "shielded" moisture sensor signal. In some embodiments, a "non-shielded" moisture sensor signal may comprise a radio frequency signal. In some embodiments, a reader may generate an audible or visible indication signal in response to a "non-shielded" moisture sensor signal, while in other embodiments a reader may generate an indication signal which is a non-signal or silence in response to a "non-shielded" moisture sensor signal. In some embodiments, a "shielded" moisture sensor signal, which may indicate the presence of moisture, can result in a non-audible or non-visible indication signal generated by the reader and a "non-shielded" moisture sensor signal, which may indicate the lack of moisture (or the lack of some level of moisture), can result in an audible or visible indication signal generated by the reader.

Methods disclosed herein can also be utilized in situations where the moisture sensor, once subjected to a moist atmosphere is then exposed to drying conditions. Drying conditions may include an atmosphere that has a lower relative humidity than one previously encountered, or active drying conditions such as heat, air flow, etc. A step of subjecting a moisture sensor to drying conditions can serve different purposes. For example, a method can be carried out to determine if the drying conditions are sufficient to dry the environment including the moisture sensor to a desired level. In such instances, subjecting the moisture sensor to the drying conditions can be carried out before or after the reader interrogates the moisture sensor. Methods disclosed herein can also be utilized in situations where the moisture sensor is not subjected to drying conditions.

Figure 6:
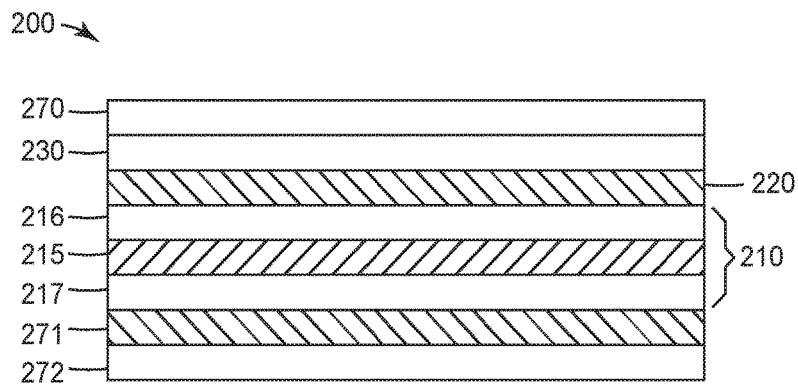
FIG. 6 is a cross-sectional view of another embodiment of a disclosed moisture sensor.

FIG. 6 is a cross-sectional view of another embodiment of a disclosed moisture sensor. The moisture sensor 200 in FIG. 6 includes a resonant circuit 210, an optional insulative layer 220, a conditionally conductive layer 230, and a second optional insulative layer 270. The moisture sensor 200 can also include an optional adhesive layer 271 and an optional release liner 272. In the embodiment depicted herein, the resonant circuit 210 can include a coil 216, a substrate 215, and a connector 217. The substrate 215 can include, for example a polymer film, polyester for example. In some embodiments, the resonant circuit 210, the optional adhesive layer 271, and the optional release liner 272 can all be part of a commercially available RFID tag or EAS tag. Upon use, the optional release liner 272 can be peeled away from the moisture sensor and the moisture sensor can be adhered to an article via the optional adhesive layer 271.

Suitable adhesives for use in disclosed moistures sensors, packages, and methods described herein may include pressure-sensitive adhesives, repositionable adhesives, heat-bondable adhesives, hot-melt adhesives, and other adhesives known in the art. Illustrative pressure-sensitive adhesives can include water-resistant pressure sensitive adhesive such as cross-linked acrylics, tackified rubber adhesives (e.g. natural rubber polyisoprene styrene butadiene rubber), and the like. Illustrative repositionable adhesives can include those described in U.S. Pat. No. 6,905,763. Other illustrative adhesives can include adhesives based on acrylic, urethane, and silicone polymers, polyurethanes, styrene block copolymers, polycarbonates, fluoropolymers, silicone rubbers, polyamides, polyesters, polyolefins, and ethyl-vinyl acetate copolymers. Useful adhesives can optionally be able to withstand the temperatures, pressures, and moisture levels of steam sterilization processes. In some embodiments, the adhesives can be moisture-permeable. In some embodiments, the adhesive can be clear, transparent, or sheer. One skilled in the art can readily select adhesives appropriate for the desired use.

Disclosed moisture sensors, systems, and methods can be used in a number of applications, including but not limited to bioanalytical applications, consumer applications such as water-absorbing systems or consumer electronics, medical devices, sterilization processes, etc. The remote sensing capabilities of disclosed systems and methods can be advantageously utilized for monitoring processes involving articles that are sealed, for example sterilization packs or packaged electronics. Disclosed devices, systems, and methods can be advantageously utilized for monitoring the moisture conditions of sealed articles because the interior of article can be determined to be dry or not dry without breaking the seal of article.

Disclosed sensors, systems and/or methods could also be configured to be utilized in automated processes, where the sensor can be monitored to therefore allow automated control of a number of steps and/or conditions. Conditions that can be monitored for by utilizing disclosed sensors and/or methods can include: does the article include a disclosed sensor (e.g., was the article prepared correctly for the particular process by including a disclosed sensor), has the sensor and/or the article including the sensor become "wet" (e.g., was the article subjected to a specific level of moisture for the particular process), and has the sensor and/or the article been sufficiently dried (e.g., if a drying step is present, was the drying step successful?).

In some embodiments, an indication of "not-dry" when checking to determine if the sensor and/or article are dry could lead to further (e.g., automatically controlled) drying of the article to be dried. A reader (of a disclosed system) could be configured to sequentially check the status ("dry" or "not dry") of the article to be dried while drying is occurring in order to most efficiently complete a drying process (e.g., no more energy, time, or both would be wasted drying than would be necessary to reach a desired level of dryness). Automated systems could also control the dry time and conditions, control how often sensors are checked, or any combination thereof.

In some embodiments, disclosed moisture sensors can be attached to a base layer or to a portion of an enclosure comprising a moisture-permeable material. Attachment of a moisture sensor to the base layer or moisture-permeable material is generally facilitated through bonding by the use of adhesives, extrusion processes, ultrasonic bonding, or other appropriate attachment mechanisms know in the art, or through an option adhesive layer (e.g., optional adhesive layer 271 in FIG. 6). The attachment method, particularly the adhesives, should be compatible with whatever conditions the article or process presents.

Following are exemplary embodiments of devices, systems, and methods according to aspects of the present invention.

Embodiment 1 is a moisture sensor comprising a resonant circuit having a resonant frequency and comprising a capacitive element and an inductive element, wherein the inductive element acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer.

Embodiment 2 is a moisture sensor according to embodiment 1, wherein the moisture sensor is reversible.

Embodiment 3 is a moisture sensor according to any of the preceding embodiments, wherein the conditionally conductive polymeric layer is a hydrogel.

Embodiment 4 is a moisture sensor according to embodiment 3, wherein the hydrogel is premoistened.

Embodiment 5 is a moisture sensor according to any of the preceding embodiments, wherein the conditionally conductive polymeric layer comprises more than one layer.

Embodiment 6 is a moisture sensor according to any one of the preceding embodiments, wherein the polymeric layer comprises a pressure-sensitive adhesive having a polymeric matrix comprised of copolymers of hydrogen bond donating monomers and hydrogen bond accepting monomers.

Embodiment 7 is a moisture sensor according to any one of the preceding embodiments, wherein the polymeric layer comprises a pressure-sensitive adhesive having a polymeric matrix comprised of copolymers of acrylic acid and N-vinylpyrrolidone.

Embodiment 8 is a moisture sensor according to any one of the preceding embodiments, wherein the conditionally conductive polymeric layer quantitatively changes from a first level of conductivity to a second level of conductivity when exposed to a relative humidity ranging from about 55% to about 95% relative humidity at 23° C.

Embodiment 9 is a moisture sensor according to any one of the preceding embodiments, wherein the sensor further comprises one or more layers selected from the group consisting of adhesives, films, paper, ink, and combinations thereof.

Embodiment 10 is a moisture sensor according to any one of the preceding embodiments, wherein the polymeric layer has a threshold conductivity at which the polymeric layer acts as a magnetic shield for the resonant circuit when exposed to a threshold set of moisture conditions.

Embodiment 11 is a moisture sensor according to any one of the preceding embodiments, wherein the conditionally conductive polymeric layer further comprises a salt.

Embodiment 12 is a system comprising the moisture sensor according to any one of the preceding embodiments; and a reader configured to transmit a reader radio frequency signal to the resonant circuit of the moisture sensor at or near the resonant frequency of the resonant circuit, and wherein the reader is further configured to receive a moisture sensor signal transmitted by the resonant circuit.

Embodiment 13 is a system according to embodiment 12, wherein the moisture sensor signal is selected from a radio frequency signal and a non-signal.

Embodiment 14 is a system according to any one of embodiments 12 or 13, wherein the reader is further configured to generate an indication signal based on the moisture sensor signal received from the resonant circuit.

Embodiment 15 is a system according to any one of embodiments 12-14, wherein the reader is configured to receive a first moisture sensor signal from the resonant circuit of the moisture sensor when the moisture sensor is at a first set of moisture conditions and a second moisture sensor signal from the resonant circuit of the moisture sensor when the moisture sensor is at a second set of moisture conditions.

Embodiment 16 is a system according to embodiment 14, wherein at least one of the first moisture sensor signal and second moisture sensor signal is a non-signal.

Embodiment 17 is a method of detecting moisture comprising sequential steps: (a) exposing a moisture sensor to a moist atmosphere, wherein the moisture sensor comprises a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer; (b) transmitting a reader radio frequency signal from a reader to the resonant circuit of the moisture sensor at the resonant frequency of the resonant circuit to produce a moisture sensor signal, wherein the reader is configured to transmit a reader radio frequency signal to the resonant circuit of the moisture sensor at or near the resonant frequency of the resonant circuit; (c) receiving, with the reader, a moisture sensor signal from the moisture sensor and generating, with the reader, an indication signal based on the moisture sensing signal received from the resonant circuit, wherein the reader is further configured to receive a moisture sensor signal transmitted by the resonant circuit and generate an indication signal based on the moisture sensor signal received; and (d) determining a level of moisture within the moist atmosphere based on the signal generated by the reader.

Embodiment 18 is a method according to embodiment 17, further comprising the step:

(a1) exposing the moisture sensor to drying conditions to at least partially dry the moisture sensor; wherein step (a1) occurs after step (a) and before step (b).

Embodiment 19 is a method according to any one of embodiments 17 or 18, wherein determining the level of moisture within the moist atmosphere is further based on the known humidity sensitivity of the conditionally conductive polymeric layer of the moisture sensor.

Embodiment 20 is a method according to any one of embodiments 17 to 19, wherein the indication signal is a non-signal.

Embodiment 21 is a method comprising receiving, by a receiving device, a moisture sensor signal produced by a moisture sensor, the moisture sensor comprising a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions; and an insulative layer disposed between the resonant circuit and the conditionally conductive polymeric layer; and determining the moisture conditions to which the polymeric layer is exposed based on the moisture sensor signal received by the receiving device.

EXAMPLES

Objects and advantages are further illustrated by the following examples, but the particular materials and amounts thereof recited in these examples, as well as other conditions and details, should not be construed to unduly limit this disclosure.

Unless otherwise noted herein, a SenTech 9.5 MHz Portable Hand Verifier, model STC311 (from SenTech EAS Corporation (Pompano Beach, Fla.) reader was utilized to obtain readings from all sensors herein.

Example 1—Preparation of Moisture Sensors

Moisture Sensor Version 1 (MSV1)

The SL595P sensor label, commercially available from SenTech EAS Corporation, was used to prepare MSV1 of Example 1. The SL595P sensor label is tuned to a frequency of 9.5 MHz and is non-deactivatable; a plain white label compatible with detector devices such as all SenTech 9.5 MHz RF systems as well as any competitive 9.5 MHz RF systems using labels. The SL595P label measures 2.05"× 1.90" (52×48 mm) and is provided rolled in quantities of 2000 labels units per roll. In the Examples below a reader, a SenTech 9.5 MHz Portable Hand Verifier, model STC311 (from SenTech EAS Corporation (Pompano Beach, Fla.) was used to interrogate the sensors.

MSV1 moisture sensors were prepared as "salt imbibed" sensors in the following manner. The roll of SL595P sensor labels was unwound from the release liner. With the sensor label adhesive exposed face up, sodium chloride (MORTON brand table salt) was shaken onto the adhesive using a particle loading hopper system that vibrated to distribute the sodium chloride onto the adhesive side of the sensor label. The calculated coating weight was 0.5 grams per meter square. After the salt was applied, a paper towel layer was laminated onto the salt coated adhesive. The paper towel used was KIMBERLY-CLARK PROFESSIONAL 01000 SCOTT High-Capacity Towel Roll White Hard Roll Towel slit to 7.6 cm wide. The salt imbibed tags of MSV1 were then rolled up onto a 7.6 cm core.

Moisture Sensor Version 2 (MSV2)

MSV2 was prepared in a similar fashion as MSV1, above, except that sodium chloride salt was not added to the adhesive side of the SL595P label and instead a hydrogel adhesive, AG603-6 sensing gel (available from AmGel Technologies a division of Axelgaard Manufacturing Company Ltd. of Fallbrook, Calif.) was placed in contact with the adhesive surface of the SL595P label. The exposed hydrogel surface was then adhered to a sheet of printer copy paper (STAPLES Copy Paper, Item: 135848 Model: 135848-WH. Framingham, Mass.), and MSV2 sensors were then cut to the size of the original SL595P label sensors.

Moisture Sensor Version 3 (MSV3)

MSV3 was prepared in a similar fashion as MSV2, above, except that the AG603-6 sensing gel hydrogel adhesive was not used. The hydrogel adhesive of 3M RED DOT Resting Electrode 2330 (available from 3M Company, St. Paul, Minn.) was used instead of the AG603-6 sensing gel. The 3M hydrogel was placed in contact with the adhesive surface of the SL595P label. Similarly to MSV2 the exposed hydrogel surface was then adhered to a sheet of printer copy paper and the MSV3 sensors were cut to the size of individual sensors.

Example 2—Detection of MSV1 Before and after Steam Sterilization with Adequate Dry Cycle MSV1 was placed between two stacks of printer paper cut to 10×10 cm (4×4 inch) dimensions. Each stack was 15 sheets of printer paper, approximately 6.4 mm (0.25 inch) thick held together with two staples on opposite sides of the MSV1. The assembly was placed in the center position of a sterilization wrap (KC600 KIMGUARD ONE-STEP Sterilization Wrap, available from Kimberly-Clark Health Care of Roswell, Ga.) with the salt-imbibed paper towel surface facing "up". An empty aluminum container available from 3M Orthopedics with approximate dimensions 36×23×9 cm (14×9×3.5 inches), used as a surrogate for an instrument tray, was placed on top of the MSV1 printer paper enveloped assembly. The aluminum container was then wrapped in a fashion typically done in preparing an article for sterilization, and taped closed using 3M autoclave tape 1322. A 9.5 MHz RF detector device (SenTech 9.5 MHz Portable Hand Verifier, model STC311 from SenTech EAS Corporation (Pompano Beach, Fla.)) was used to detect the condition of the dry MSV1 copy paper assembly before the sensor was exposed to the sterilization cycle. When the sensor is dry it is functional and an audible "beep" is generated by the detection device.

The wrapped article, comprising the MSV1 copy paper assembly and the aluminum container, was placed into an autoclave ((AMSCO Eagle Series, 3013-C Vacamatic, chamber size: 41×41×66 cm) and subjected to a 132° C., 4 minute steam and 30 minutes dry cycle. After removing the wrapped article from the autoclave, the detector device was used again to verify the MSV1 was dry and functional, as indicated by the audible "beep" sound from the detector. The Example 2 showed that the dry MSV1 could be detected before and after sterilization, indicating a "dry pack" as expected after this adequately dried sterilization cycle.

Example 3—Use of Moisture Sensor to Detect Wet Pack after Steam Sterilization with Inadequate Dry Cycle For Example 3 the same procedure as Example 2 was repeated to prepare a new MSV1 copy paper assembly positioned beneath an aluminum container, wrapped with the KC600 sterilization wrap and taped closed with 3M autoclave tape 1322. The wrapped article was placed into an autoclave (GETINGE Model AC1, chamber size: 66×66×66 cm, obtained from Getinge USA, Inc. of Rochester, N.Y.)) and subjected to a 135° C., 10 minute steam and a 1 second dry cycle. This inadequate drying time was known to result in "wet packs". After removal of the wrapped article comprising the MSV1 assembly, the detection device was used to interrogate the moisture condition of the MSV1. There was no audible "beep" from the detection device, which indicated the pack was "WET".

Next the wrapped article was opened and the wet MSV1 assembly was removed and allowed to air dry overnight. After air drying overnight, the MSV1 assembly was interrogated with the detection device and an audible "beep" signal was perceived, confirming that the sensor was still functional, once fully dried.

Example 4—Use of Moisture Sensor in One of Three Locations to Detect Wet Pack

The ability of the electronic moisture sensor to detect wet packs when placed at various locations in the wrapped article was further tested. The sterilization cycle parameters used in the Example 4 testing included a steam sterilization cycle of 132° C. for 4 minutes followed by a 40-minute dry time. MSV2 sensors were prepared as described above, and tested by placing them at various positions within a wrapped article and under a variety of test conditions and configurations as described below. The following definitions apply to the descriptions used in Tables 2-6, below.

"Load Size" indicated the relative fullness of the sterilization chamber used in the study. The "full" load used a small chambered GETINGE sterilizer (GETINGE Model 410 AC1, chamber size: 41×41×41 cm), which was filled with three items: an unwrapped aluminum rigid container, weighing 5.07 Kg (article 1), and two instrument sets: a small wrapped instrument set (article 2) and a large wrapped instrument set (article 3). The "half" load used a large chambered GETINGE sterilizer (GETINGE Model AC1, chamber size: 66×66×66 cm), which was filled with the same three items: an unwrapped aluminum rigid container (article 1), and two instrument sets: a small wrapped instrument set (article 2) and a large wrapped instrument set (article 3).

"Tray Size" indicated the use of either the small, wrapped 36×23×9 cm aluminum container with no tray, weighing 5.55 Kg, perforated over its surface by 6.4 mm holes (article 2) or the large, wrapped 25×46×13 cm anodized aluminum container, with a tray, weighing 8.33 Kg, perforated over its surfaces by 12.7 mm holes (article 3). One of either article 2 or article 3 included the MSV2 sensors being evaluated, positioned as described below.

"Wrap Type" denoted the use of a single layer of either KC300 KIMGUARD ONE-STEP Sterilization Wrap or KC500 KIMGUARD ONE-STEP Sterilization Wrap (Kimberly Clark).

"Silicone Mat" denoted the use of a silicone mat on which was placed the article (2 or 3) containing the MSV2 sensors.

"Wet Pack Process Step" indicated an additional method used to attempt to induce a wet pack.

One process step was placing the sterilized article onto a metal cart surface at room temperature immediately after the sterilization and dry cycle was complete and allowing the article to stand for 10 minutes before interrogating the MSV2 sensors for wetness. This process step was called "move to cold surface." In another process step a reduced post-sterilization vacuum (0.328 bar) was used during the dry cycle, called "reduced post vacuum pulse." In some instances, "5 min dry time" indicated a 5 minute dry time was used instead of a 40 minute dry time.

"Signal?" indicated YES or NO that an audible "beep" was emitted by the detection device when interrogating the WPSV2 placed at one of the three locations TOP, SIDE or BOTTOM. A result of YES indicated an audible "beep" was perceived and thus the MSV2 was dry and functional. A result of NO indicated an audible "beep" was not perceived and therefore the MSV2 circuit was shielded and the MSV2 was considered wet.

"Top" indicated the MSV2 was placed between the top surface of the sterilization container and a flap of sterilization wrap. Such a flap is a feature of wrapping according to the well-known "envelope style" of packaging instruments for surgery and is used to open the wrapped container in the operating room (OR). As such, the sensor on top lies between a layer of sterilization wrap that covers the top of the metal container and a layer of sterilization wrap that forms a "flap" that serves as a handle for removing the wrap from the container and exposing the container during opening in the operating room.

"Side" indicated the MSV2 was sandwiched between a side panel of the aluminum rigid container and the sterilization wrap such that the printer paper portion of the moisture sensor faced the side of the container.

"Bottom" indicated that the 52×48 mm MSV2 was placed between a linen towel and the bottom of the instrument set; either the small instrument set (article 2) or the large instrument set (article 3) the with the printer paper side of the MSV2 facing "up." The linen towels used were Medline O.R. Towels—Sterile Virgin O.R. Towels, Blue, 41×66 cm (16×26 inches), Pre-Washed, De-Linted, Folded, Packaged & Sterilized, product number MDT2168204, available from Medline Industries Inc. The linen towel, the MSV2 sensor, and metal container being stacked in that order in the center of a flat, open sheet of the select KC sterilization wrap. When wrapped, the bottom portion of the metal sterilization container touched both the printer paper side of the MSV2 and the periphery of the linen towel positioned under the sensor.

"Damp Towel?" indicated the dampness or moisture feel of the linen towel after the sterilization process. The dampness feel is a subjective evaluation. Therefore, in an attempt to correlate the dampness feel to a weight percent change, the following evaluation was performed. Seven identical linen towels were loaded with 7 different amounts of water to create a range of dampness or moisture. A trained sterile processing department (SPD) manager was asked to feel each towel and determine whether the towel would be considered "wet" or "dry", in her facility. The towels were pre-loaded with the following percentage weights of water and stored in closed plastic bags until the assessment. As shown in Table 1 below, the linen towels that had greater than about 6% moisture content (weight water/weight of towel, expressed as percentage) were deemed to be "wet" by the SPD manager.

TABLE 1

Damp Towel Feel Evaluation

| % Water in Towel | 0% | 3.40% | 4.70% | 6.41% | 8.70% | 12.70% | 24.20% |
|---|---|---|---|---|---|---|---|
| Evaluation | Dry | Dry | Dry | Wet | Wet | Wet | Wet |

"Wt % Water in towel" indicated the actual measured weight percent of water in the towel after being processed in the sterilization experiment.

"Determined DRY or WET PACK", indicated if a pack was ultimately considered to be a DRY PACK or a WET PACK based on a plurality of observed results including: visible moisture on the wrap, visible moisture in the tray, dampness (by touch) of the towel, and percent change in towel weight (water absorption). At least 2 of the 4 results needed to indicate moisture in order for a pack to be determined a WET PACK.

TABLE 2

Test Conditions and Results of Example 4

| CONDITIONS | Example 4A | Example 4B | Example 4C | Example 4D | Example 4E |
|---|---|---|---|---|---|
| Load Size | full | half | half | full | half |
| Tray Size | large | small | large | large | large |
| Wrap type | KC500 | KC300 | KC500 | KC300 | KC300 |
| Silicone Mat | present | absent | absent | absent | present |
| Wet Pack Process Step | Move to cold surface | Move to cold surface | Move to cold surface | Move to cold surface | Move to cold surface |
| RESULTS | | | | | |
| Moisture on Wrap? | YES | YES | YES | YES | YES |
| Moisture in Tray? | NO | NO | NO | NO | YES |
| Damp Towel? | NO | NO | NO | NO | NO |
| Wt % Water in towel | 3.4% | 3.6% | 3.7% | 3.5% | 2.8% |
| Signal - Top? | YES | YES | YES | YES | NO |
| Signal - Side? | YES | YES | YES | YES | NO |
| Signal - Bottom? | NO | YES | NO | NO | NO |
| Determined DRY or WET PACK | DRY | DRY | DRY | DRY | WET |

TABLE 3

Test Conditions and Results of Example 4, continued.

| CONDITIONS | Example 4F | Example 4G | Example 4H | Example 4I | Example 4J |
|---|---|---|---|---|---|
| Load Size | half | full | full | full | half |
| Tray Size | small | small | small | large | small |
| Wrap type | KC500 | KC300 | KC500 | KC500 | KC300 |
| Silicone Mat | present | present | absent | present | absent |
| Wet Pack Process Step | Move to cold surface | Move to cold surface | Move to cold surface | Reduced post vacuum pulse | Reduced post vacuum pulse |
| RESULTS | | | | | |
| Moisture on Wrap? | YES | YES | YES | YES | YES |
| Moisture in Tray? | NO | NO | NO | YES | NO |
| Damp Towel? | NO | NO | NO | YES | NO |
| Wt % Water in towel | 2.5% | 2.4% | 2.3% | 4.2% | 1.9% |
| Signal - Top? | YES | YES | YES | YES | YES |
| Signal - Side? | YES | YES | YES | NO | YES |
| Signal - Bottom? | YES | YES | YES | NO | YES |
| Determined DRY or WET PACK | DRY | DRY | DRY | WET | DRY |

TABLE 4

Test Conditions and Results of Example 4, continued.

| CONDITIONS | Example 4K | Example 4L | Example 4M | Example 4N | Example 4O |
|---|---|---|---|---|---|
| Load Size | half | full | half | half | full |
| Tray Size | large | large | large | small | small |
| Wrap type | KC500 | KC300 | KC300 | KC500 | KC300 |
| Silicone Mat | absent | absent | present | present | present |
| Wet Pack Process Step | reduced post vac pulse | reduced post vac pulse | reduced post vac pulse | reduced post vac pulse | reduced post vac pulse |
| RESULTS | | | | | |
| Moisture on Wrap? | YES | YES | NO | NO | YES |
| Moisture in Tray? | NO | NO | NO | NO | NO |
| Damp Towel? | NO | NO | NO | NO | NO |
| Wt % Water in towel | 2.6% | 2.9% | 2.3% | 2.1% | 0.0% |
| Signal - Top? | YES | YES | YES | YES | YES |
| Signal - Side? | YES | YES | YES | YES | YES |
| Signal - Bottom? | NO | NO | YES | YES | NO |
| Determined DRY or WET PACK | DRY | DRY | DRY | DRY | DRY |

TABLE 5

Test Conditions and Results of Example 4, continued.

| CONDITIONS | Example 4P | Example 4Q | Example 4R | Example 4S | Example 4T |
|---|---|---|---|---|---|
| Load Size | full | full | half | half | full |
| Tray Size | small | large | small | large | large |
| Wrap type | KC500 | KC500 | KC300 | KC500 | KC300 |
| Silicone Mat | absent | present | absent | absent | absent |
| Wet Pack Process Step | reduced post vac pulse | 5 min dry time | 5 min dry time | 5 min dry time | 5 min dry time |
| RESULTS | | | | | |
| Moisture on Wrap? | YES | YES | YES | YES | YES |
| Moisture in Tray? | NO | YES | NO | YES | YES |
| Damp Towel? | NO | YES | YES | YES | YES |
| Wt % Water in towel | 2.5% | 44.6% | 16.5% | 32.7% | 43.0% |

TABLE 5-continued

Test Conditions and Results of Example 4, continued.

| CONDITIONS | Example 4P | Example 4Q | Example 4R | Example 4S | Example 4T |
|---|---|---|---|---|---|
| Signal - Top? | YES | NO | NO | NO | NO |
| Signal - Side? | YES | NO | NO | NO | NO |
| Signal - Bottom? | YES | NO | NO | NO | NO |
| Determined DRY or WET PACK | DRY | WET | WET | WET | WET |

TABLE 6

Test Conditions and Results of Example 4, continued.

| CONDITIONS | Example 4U | Example 4V | Example 4W | Example 4X |
|---|---|---|---|---|
| Load Size | half | half | full | full |
| Tray Size | large | small | small | small |
| Wrap type | KC300 | KC500 | KC300 | KC500 |
| Silicone Mat | present | present | present | absent |
| Wet Pack | 5 min | 5 min | 5 min | 5 min |
| Process Step | dry time | dry time | dry time | dry time |
| Moisture on Wrap? | YES | YES | YES | YES |
| Moisture in Tray? | YES | YES | YES | NO |
| Damp Towel? | YES | YES | YES | YES |
| Wt % Water in towel | 62.6% | 27.4% | 20.4% | 19.2% |
| Signal - Top? | NO | NO | NO | NO |
| Signal - Side? | NO | NO | NO | NO |
| Signal - Bottom? | NO | NO | NO | NO |
| Determined DRY or WET PACK | WET | WET | WET | WET |

The results of Example 4, shown in Tables 2-6, indicate that the MSV2 can properly indicate a wet pack consistent with manual observations, when placed on either the side or the bottom of the wrapped article.

Example 5—Comparison of MSV2 and MSV3 to Comparative Moisture Sensor CMS1

Comparative Moisture Sensor (CMS1)

Comparative moisture sensor CMS1 was prepared by using the SL595P sensor label and integrating it with a 5×5 cm portion cut from a commercially available diaper (COMFORT-AIRE brand disposable briefs, size regular, available from Medline Industries Inc.), containing a super absorbent polymer (SAP). The diaper interior side was dry loaded with 500 milligrams of sodium chloride before the adhesive side of the sensor was brought into contact with the salt loaded diaper with SAP.

MSV2 and MSV3 were evaluated under the following conditions to a prepared comparative moisture sensor CMS1. First, the MSV2, MSV3 and CMS1 units were all dried for 16 hours at 45° C. Next, all the MSV2, MSV3 and CMS units were placed together in a large aluminum pan placed in the center of a first humidity chamber at 23° C. and 54% relative humidity and interrogated periodically to determine if each sensor was shielded (or in the case of the CMS1), indicated by the lack of an audible "beep" from the detection device (NON-SIGNAL), or not shielded, indicated by an audible "beep" from the detection device (SIGNAL). Following the first humidity chamber the MSV2, MSV3 and CMS1 units were all transferred immediately to a second humidity chamber at 49° C. and 90% relative humidity and checked after 10 minutes. Finally, after removing all the units from the second humidity chamber and placing them at ambient room temperature and humidity conditions, the CMS1 was confirmed operational to detect liquid by adding 10 mL water directly on the sensor and interrogating with the detection device.

TABLE 7

Results of Example 5, Humidity Chamber Testing

| Time & Conditions | MSV2 1 unit | MSV3 3 units | CMS1 2 units |
|---|---|---|---|
| 1 hour @ 23° C. and 54% RH | SIGNAL | SIGNAL | SIGNAL |
| 2 hours @ 23° C. and 54% RH | SIGNAL | SIGNAL | SIGNAL |
| 20 hours @ 23° C. and 54% RH | SIGNAL | SIGNAL | SIGNAL |
| 10 minutes @ 49° C. and 90% RH | NON-SIGNAL | NON-SIGNAL | SIGNAL |
| Direct addition of 10 mL water | — | — | NON-SIGNAL |

The results of Example 5, shown in Table 7, indicates that MSV2 and MSV3 are more sensitive than the CMS1 and can indicate wetness in a high humidity environment, whereas the CMS1 must be in direct contact with liquid water in order to indicate wetness.

Example 6—Comparison of MSV1 and MSV2 to CMS1

Samples of MSV1 and MSV2 and CMS1 were evaluated under the following conditions to compare their respective sensitivity to moisture in the form of % RH and liquid water. First, all the samples were dried overnight in an oven at 45° C. Next, all the samples of MSV1 (2 units), MSV2 (3 units) and CMS1 (1 unit) were placed together (spread out in a large flat aluminum pan) in a controlled humidity chamber at a target percent relative humidity (% RH) of 30% and 25° C., where they were allowed to equilibrate for 48 hours. The controlled humidity and temperature chamber was a model SM-8-3800, available from Thermotron Industries (Holland, Mich., USA). After the equilibration period, the samples of MSV1, MSV2 and CMS1 were all interrogated with the reader/detector and all were dry (non-shielded) and functional, as indicated by the audible "beep" sound from the reader/detector. The chamber setting was then immediately changed to the next target % RH and the samples were allowed to equilibrate until the next reading. This process was repeated, stepping up the % RH and interrogating the samples after a period of equilibration at the set point % RH. The chamber typically reached the target % RH within 20 minutes. Table 8 indicates the conditions and results for Example 6, for MSV1, MSV2, and CMS1. The target % RH test points were 30% RH, 40% RH, 50% RH, 60% RH, 70% RH, and 85% RH. The actual measured % RH as indicated by the calibrated chambers are shown in Table 8. Finally, after exposing all the samples to the highest humidity, the samples were removed from the humidity chamber and the MSV1 and CMS1 sensors were confirmed operational to detect liquid by adding 10 mL water directly onto the sensors and interrogating with the detection device. Only after the direct addition of water did the MSV1 and CMS1 sensors indicate shielding (NON-SIGNAL).

TABLE 8

Results of Example 6, Additional Humidity Chamber Testing at 25° C.

| Actual % RH | Equilibration hours | MSV1-1 | MSV1-2 | MSV2-1 | MSV2-2 | MSV2-3 | CMS1 |
|---|---|---|---|---|---|---|---|
| 32.8 | 48 | SIGNAL | SIGNAL | SIGNAL | SIGNAL | SIGNAL | SIGNAL |
| 44.2 | 24 | SIGNAL | SIGNAL | SIGNAL | SIGNAL | SIGNAL | SIGNAL |
| 53.0 | 72 | SIGNAL | SIGNAL | SIGNAL | SIGNAL | SIGNAL | SIGNAL |
| 58.2 | 96 | SIGNAL | SIGNAL | NON-SIGNAL | NON-SIGNAL | NON-SIGNAL | SIGNAL |
| 68.2 | 48 | SIGNAL | SIGNAL | NON-SIGNAL | NON-SIGNAL | NON-SIGNAL | SIGNAL |
| 85.8 | 120 | SIGNAL | SIGNAL | NON-SIGNAL | NON-SIGNAL | NON-SIGNAL | SIGNAL |
| water added directly to sensor | N/A | NON-SIGNAL | NON-SIGNAL | Not tested | Not tested | Not tested | NON-SIGNAL |

The complete disclosure of the patents, patent documents, and publications cited in the Background, the Detailed Description, and elsewhere herein are incorporated by reference in their entirety as if each were individually incorporated These and other variations and modifications of the disclosure will be apparent to those skilled in the art without departing from the scope of the disclosure, and it should be understood that this disclosure is not limited to the illustrative embodiments set forth herein. Accordingly, the disclosure is to be limited only by the claims provided below and equivalents thereof.

The invention claimed is:

1. A moisture sensor comprising:
a resonant circuit having a resonant frequency and comprising a capacitive element and an inductive element, wherein the inductive element acts as an antenna;
a conditionally conductive polymeric layer, wherein the conditionally conductive polymeric layer has a first level of conductivity when exposed to a first set of moisture conditions and has a second level of conductivity when exposed to a second set of moisture conditions, wherein the conditionally conductive polymeric layer has a threshold conductivity at which the conditionally conductive polymeric layer acts as a magnetic shield for the resonant circuit when exposed to a threshold set of moisture conditions; and
an insulative layer disposed between the resonant circuit and the conditionally conductive polymeric layer,
wherein the moisture sensor can be used more than once.

2. The moisture sensor of claim 1, wherein the moisture sensor is reversible.

3. The moisture sensor of claim 1, wherein the conditionally conductive polymeric layer is a hydrogel.

4. The moisture sensor of claim 3, wherein the hydrogel is premoistened.

5. The moisture sensor of claim 1, wherein the conditionally conductive polymeric layer comprises more than one layer.

6. The moisture sensor of claim 1, wherein the polymeric layer comprises a pressure-sensitive adhesive having a polymeric matrix comprised of copolymers of hydrogen bond donating monomers and hydrogen bond accepting monomers.

7. The moisture sensor of claim 1, wherein the polymeric layer comprises a pressure-sensitive adhesive having a polymeric matrix comprised of copolymers of acrylic acid and N-vinylpyrrolidone.

8. The moisture sensor of claim 1, wherein the conditionally conductive polymeric layer quantitatively changes from a first level of conductivity to a second level of conductivity when exposed to a relative humidity ranging from about 55% to about 95% relative humidity at 23° C.

9. The moisture sensor of claim 1, wherein the sensor further comprises one or more layers selected from the group consisting of adhesives, films, paper, ink and combinations thereof.

10. The moisture sensor of claim 1, wherein the conditionally conductive polymeric layer further comprises a salt.

11. A system comprising:
the moisture sensor of claim 1; and
a reader configured to transmit a reader radio frequency signal to the resonant circuit of the moisture sensor at least at the resonant frequency of the resonant circuit, and wherein the reader is further configured to receive a moisture sensor signal transmitted by the resonant circuit.

12. The system of claim 11, wherein the moisture sensor signal is selected from a radio frequency signal and a non-signal.

13. The system of claim 11, wherein the reader is further configured to generate an indication signal based on the moisture sensor signal received from the resonant circuit.

14. The system of claim 11, wherein the reader is configured to receive a first moisture sensor signal from the resonant circuit of the moisture sensor when the moisture sensor is at a first set of moisture conditions and a second moisture sensor signal from the resonant circuit of the moisture sensor when the moisture sensor is at a second set of moisture conditions.

15. The system of claim 13, wherein at least one of the first moisture sensor signal and second moisture sensor signal is a non-signal.

16. A method of detecting moisture comprising sequential steps:
(a) exposing a moisture sensor to a moist atmosphere, wherein the moisture sensor comprises a resonant circuit having a resonant frequency and comprising a capacitive element and an inductive element that acts as an antenna; a conditionally conductive polymeric layer, wherein the conditionally conductive polymeric layer has a first level of conductivity when exposed to a first set of moisture conditions and has a second level of conductivity when exposed to a second set of moisture conditions, wherein the conditionally conductive polymeric layer has a threshold conductivity at which the conditionally conductive polymeric layer acts as a magnetic shield for the resonant circuit when exposed to a threshold set of moisture conditions; and an insulative layer disposed between the resonant circuit and the conditionally conductive polymeric layer;

(b) transmitting a reader radio frequency signal from a reader to the resonant circuit of the moisture sensor at the resonant frequency of the resonant circuit to produce a moisture sensor signal, wherein the reader is configured to transmit a reader radio frequency signal to the resonant circuit of the moisture sensor at least at the resonant frequency of the resonant circuit;

(c) receiving, with the reader, a moisture sensor signal from the moisture sensor and generating, with the reader, an indication signal based on the moisture sensing signal received from the resonant circuit, wherein the reader is further configured to receive a moisture sensor signal transmitted by the resonant circuit and generate an indication signal based on the moisture sensor signal received; and (d) determining a level of moisture within the moist atmosphere based on the signal generated by the reader.

17. The method of claim 16, further comprising the step:

(a1) exposing the moisture sensor to drying conditions to at least partially dry the moisture sensor; wherein step (a1) occurs after step (a) and before step (b).

18. The method of claim 16, wherein determining the level of moisture within the moist atmosphere is further based on the known humidity sensitivity of the conditionally conductive polymeric layer of the moisture sensor.

19. The method of claim 16, wherein the indication signal is a non-signal.

20. A method comprising:

receiving, by a receiving device, a moisture sensor signal produced by a moisture sensor, the moisture sensor comprising a resonant circuit having a resonant frequency and comprising a capacitive element and an inductive element that acts as an antenna;

a conditionally conductive polymeric layer, wherein the conditionally conductive polymeric layer has a first level of conductivity when exposed to a first set of moisture conditions and has a second level of conductivity when exposed to a second set of moisture conditions, wherein the conditionally conductive polymeric layer has a threshold conductivity at which the conditionally conductive polymeric layer acts as a magnetic shield for the resonant circuit when exposed to a threshold set of moisture conditions; and an insulative layer disposed between the resonant circuit and the conditionally conductive polymeric layer; and determining the moisture conditions to which the polymeric layer is exposed based on the moisture sensor signal received by the receiving device.

* * * * *

UNITED STATES PATENT AND TRADEMARK OFFICE
CERTIFICATE OF CORRECTION

PATENT NO. : 10,161,895 B2  Page 1 of 1
APPLICATION NO. : 14/976506
DATED : December 25, 2018
INVENTOR(S) : Giuseppe Bommarito It is certified that error appears in the above-identified patent and that said Letters Patent is hereby corrected as shown below:

In the Specification

Column 5
Line 25-26, delete "polyacrylomide," and insert -- Polyacrylamide --, therefor.

Column 6
Line 8, delete "hydrocollloids" and insert -- hydrocolloids --, therefor.

Column 17
Line 14, delete "((AMSCO" and insert -- (AMSCO --, therefor.
Line 34, delete "N.Y.))" and insert -- N.Y.) --, therefor.

Signed and Sealed this
Fifteenth Day of October, 2019

Andrei Iancu
*Director of the United States Patent and Trademark Office*